(12) United States Patent
Yao et al.

(10) Patent No.: US 9,435,634 B2
(45) Date of Patent: Sep. 6, 2016

(54) DETECTION DEVICE AND METHOD

(71) Applicants: BOE Technology Group Co., Ltd., Beijing (CN); Beijing BOE Display Technology Co., Ltd., Beijing (CN)

(72) Inventors: Huali Yao, Beijing (CN); Chaoqin Xu, Beijing (CN); Liping Luo, Beijing (CN); Zengbiao Sun, Beijing (CN); Shaoshuai Mu, Beijing (CN); Huishuang Liu, Beijing (CN)

(73) Assignees: BOE Technology Group Co., Ltd., Beijing (CN); Beijing BOE Display Technology Co., Ltd., Beijing (CN)

( * ) Notice: Subject to any disclaimer, the term of this patent is extended or adjusted under 35 U.S.C. 154(b) by 0 days.

(21) Appl. No.: 14/471,279

(22) Filed: Aug. 28, 2014

(65) Prior Publication Data
US 2015/0323470 A1 Nov. 12, 2015

(30) Foreign Application Priority Data
May 7, 2014 (CN) .......................... 2014 1 0189782

(51) Int. Cl.
*G01B 11/14* (2006.01)
*G01B 11/00* (2006.01)
(Continued)

(52) U.S. Cl.
CPC ......... *G01B 11/002* (2013.01); *G01N 21/8851* (2013.01); *G01N 21/956* (2013.01); *G01N 2201/061* (2013.01); *G01N 2201/12* (2013.01)

(58) Field of Classification Search
CPC ........... G01N 21/956; G01N 21/8851; G01N 2201/061; G01N 2201/12; G01B 11/002
USPC ....................................................... 356/620
See application file for complete search history.

(56) References Cited

U.S. PATENT DOCUMENTS 4,988,198 A * 1/1991 Kondo .................. G01B 11/22
356/496
6,417,929 B1 * 7/2002 Ausschnitt et al. .......... 356/635
(Continued)

FOREIGN PATENT DOCUMENTS

| CN | 1419275 A | 5/2003 |
|---|---|---|
| CN | 101889197 A | 11/2010 |
| JP | 4496565 B2 | 7/2010 |

OTHER PUBLICATIONS

First Office Action, including Search Report, for Chinese Patent Application No. 201410189782.8, dated Mar. 7, 2016, 14 pages.

*Primary Examiner* — Kara E Geisel
*Assistant Examiner* — Hina F Ayub
(74) *Attorney, Agent, or Firm* — Westman, Champlin & Koehler, P.A.

(57) ABSTRACT

A detection device and a detection method are disclosed in the embodiments. The detection device comprises a light source, a first image information acquisition unit, a first charge coupled device (CCD), a first light splitter, and a first analyzer. The first image information acquisition unit is configured to receive a first light signal from the light source and transmit the first light signal onto a substrate, and to acquire a first image light signal generated by transmitting the first light signal onto both an edge of a first ID figure on the substrate and an edge of the substrate, and transmit the first image light signal to the first light splitter; the first light splitter is configured to transmit the first image light signal to the first CCD so that the first CCD outputs a first electrical signal; and the first analyzer is configured to receive the first electrical signal outputted from the first CCD and analyze wave crests of the first electrical signal, thereby obtaining a distance between the edge of the first ID figure on the substrate and the edge of the substrate. The detection part and detection method are used for substrate detection.

10 Claims, 4 Drawing Sheets

(51) Int. Cl.
  *G01N 21/956* (2006.01)
  *G01N 21/88* (2006.01)

(56) References Cited

U.S. PATENT DOCUMENTS

2002/0064774 A1* 5/2002 Schembri et al. ............ 435/6
2006/0082775 A1  4/2006 Fukui
2009/0051936 A1* 2/2009 Schmidt ................ G01B 21/04
                                                      356/620
2010/0124610 A1* 5/2010 Aikawa et al. .......... 427/255.28
2010/0245811 A1  9/2010 Yoshikawa
2011/0170869 A1* 7/2011 Mandai et al. ................ 398/65
2012/0294507 A1* 11/2012 Sakai et al. ................... 382/149

* cited by examiner

DETECTION DEVICE AND METHOD

CROSS-REFERENCE TO RELATED APPLICATION

This application claims the benefit of Chinese Patent Application No. 201410189782.8 filed on May 7, 2014 in the State Intellectual Property Office of China, the whole disclosure of which is incorporated herein by reference.

BACKGROUND OF THE INVENTION

1. Field of the Invention

Embodiments of the present invention relate to the field of manufacture of thin film field-effect transistor, and particularly to a detection device and a detection method.

2. Description of the Related Art

For example, the manufacture process for the thin film field-effect transistor (TFT) is complicated, and the number of types of corresponding products is large. Generally, most of products are in different processes on a product line. In order to distinguish the products, a unique identification (ID) is formed on a glass substrate.

In the conventional manufacture process, position of the identification on the glass substrate is checked only by manual sampling inspection.

SUMMARY OF THE INVENTION

The embodiments of the present invention provide a detection device and a detection method. By the detection device and the detection method according to the embodiments, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoided and the work efficiency is improved.

According to embodiments of the present invention, there is provided a detection device, comprising:

a light source, a first image information acquisition unit, a first charge coupled device (CCD), a first light splitter, and a first analyzer, wherein:

the first image information acquisition unit is configured to receive a first light signal from the light source and transmit the first light signal onto a substrate, and to acquire a first image light signal generated by transmitting the first light signal onto both an edge of a first ID figure on the substrate and an edge of the substrate, and transmit the first image light signal to the first light splitter;

the first light splitter is configured to transmit the first image light signal to the first CCD so that the first CCD outputs a first electrical signal; and the first analyzer is configured to receive the first electrical signal outputted from the first CCD and analyze wave crests of the first electrical signal, thereby obtaining a distance between the edge of the first ID figure on the substrate and the edge of the substrate.

According to embodiments of the present invention, there is provided a detection method, comprising the steps of:

receiving a first light signal from a light source by a first image information acquisition unit;

transmitting, by the first image information acquisition unit, the first light signal received from the light source onto a substrate, and acquiring, by the first image information acquisition unit, a first image light signal generated by transmitting the first light signal onto both an edge of a first ID figure on the substrate and an edge of the substrate, and transmitting, by the first image information acquisition unit, the first image light signal to a first light splitter;

transmitting, by the first light splitter, the first image light signal to a first CCD so that the first CCD outputs a first electrical signal; and analyzing the first electrical signal outputted from the first CCD, and calculating a difference between peak values of two wave crests presented in the first electrical signal, and if the difference is greater than a preset threshold value, then it is determined that a position of the first ID figure is abnormal.

DETAILED DESCRIPTION OF THE EMBODIMENTS

A further description of the invention will be made in detail as below with reference to embodiments of the present invention taken in conjunction with the accompanying drawings. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

According to an general concept of the present invention, there is provided a detection device, comprising:

a light source, a first image information acquisition unit, a first charge coupled device (CCD), a first light splitter, and a first analyzer, wherein:

the first image information acquisition unit is configured to receive a first light signal from the light source and transmit the first light signal onto a substrate, and to acquire a first image light signal generated by transmitting the first light signal onto both an edge of a first ID figure on the substrate and an edge of the substrate, and transmit the first image light signal to the first light splitter;

the first light splitter is configured to transmit the first image light signal to the first CCD so that the first CCD outputs a first electrical signal; and the first analyzer is configured to receive the first electrical signal outputted from the first CCD and analyze wave crests of the first electrical signal, thereby obtaining a distance between the edge of the first ID figure on the substrate and the edge of the substrate.

According to an general concept of the present invention, there is provided a detection method, comprising the steps of:

receiving a first light signal from a light source by a first image information acquisition unit;

transmitting, by the first image information acquisition unit, the first light signal received from the light source onto a substrate, and acquiring, by the first image information acquisition unit, a first image light signal generated by transmitting the first light signal onto both an edge of a first ID figure on the substrate and an edge of the substrate, and transmitting, by the first image information acquisition unit, the first image light signal to a first light splitter;

transmitting, by the first light splitter, the first image light signal to a first CCD so that the first CCD outputs a first electrical signal; and analyzing the first electrical signal outputted from the first CCD, and calculating a difference between peak values of two wave crests presented in the first electrical signal, and if the difference is greater than a preset threshold value, then it is determined that a position of the first ID figure is abnormal.

A further description of the invention will be made in detail as below with reference to embodiments of the present invention taken in conjunction with the accompanying drawings. In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
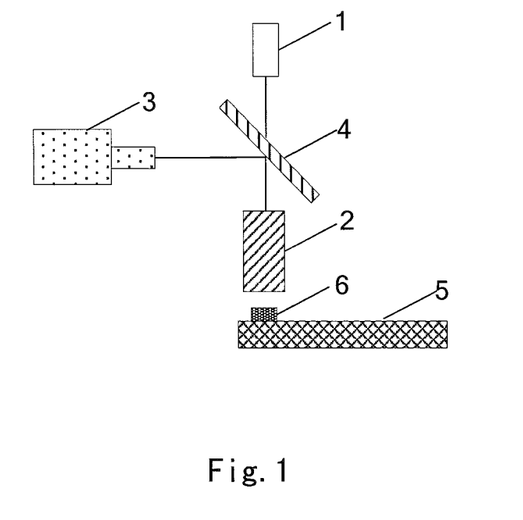
FIG. 1 is a schematic diagram showing a configuration of a detection device according to an embodiment of the present invention.

According to embodiments of the present invention, there is provided a detection device. As shown in FIG. 1, the detection device comprises: a light source 1, a first image information acquisition unit 2, a first charge coupled device (CCD) 3, a first light splitter or a first light splitting sheet 4, and a first analyzer. In the present embodiment, the first analyzer is integrated in the first CCD. Of course, a separate first analyzer may be disposed.

The light source 1 is configured to emit a light signal to provide a substrate 5 with light.

The light source may be any light source that can emit a processed beam of light. For example, the light source may be a common device having the function of a lamp house, or the like.

The first image information acquisition unit 2 may be disposed over a first ID FIG. 6 on the substrate 5. The first image information acquisition unit 2 is configured to receive a first light signal from the light source 1 and transmit the first light signal onto the substrate 5, and to acquire a first image light signal generated by transmitting the first light signal onto both an edge of the first ID FIG. 6 on the substrate and an edge of the substrate 5, and transmit the first image light signal to the first light splitter 4.

The first image information acquisition unit may be any unit that can acquire image information and transmit the acquired image information. For example, the first image information acquisition unit may be any devices, such as a camera lens, commonly used in current actual production. In other words, the first image information acquisition unit may comprise a lens or a set of lenses.

The first light splitter 4 is configured to transmit the first image light signal to the first CCD 3 so that the first CCD 3 outputs a first electrical signal.

The first analyzer is configured to receive the first electrical signal outputted from the first CCD 3 and analyze wave crests of the first electrical signal, thereby obtaining a distance between the edge of the first ID figure on the substrate and the edge of the substrate.

FIG. 1 only illustrates positions of the light source, the first light splitter, and the first CCD. In the present embodiment, the positions of the light source, the first light splitter, and the first CCD are not limited to specific positions and may be any positions so long as the functions of the light source, the first light splitter, and the first CCD can be achieved.

By detecting the position of the ID figure on the substrate by the detection device according to the embodiment of the present invention instead of manual operation, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoid and the work efficiency is improved.

Figure 2:
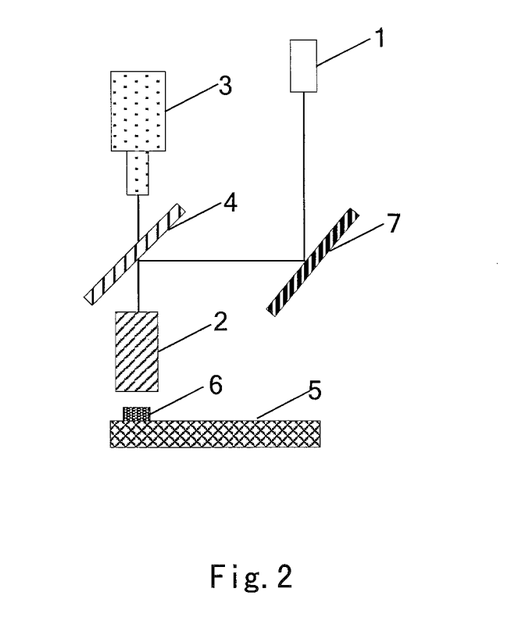
FIG. 2 is a schematic diagram showing a configuration of another detection device according to an embodiment of the present invention.

In some embodiments, referring to FIG. 2, the detection device further comprises: a first reflecting mirror 7.

The first light splitter receives the first light signal from the light source 1 through the first reflecting mirror 7. In other words, the first reflecting mirror 7 reflects the first light signal to the first light splitter 4 while the first reflecting mirror 7 filters out interference light signals from the first light signal.

The first light splitter 4 is further configured to transmit the received first light signal to the first image information acquisition unit 2.

The first reflecting mirror can filter out other interference light signals from the received first light signal such that the light onto the substrate is finally a light without interference of other light signals. In this way, it can be ensured that there is enough light on the substrate and thus the first image information acquisition unit can obtain acquire a clearer image light signal. The image light signal is transmitted to the first CCD, the first CCD outputs the first electrical signal, and the image information obtained by processing the first electrical signal by the first analyzer is clearer. As a result, the obtained light wave is clearer. Finally, the numerical value obtained by calculation by the first analyzer will be more accurate.

After the first reflecting mirror is added to the detection device, the first light splitter also needs to transmit the light signal, processed by the first reflecting mirror, to the first image information acquisition unit. At the same time, after acquiring the first image light signal, the first image information acquisition sends the light signal to the first CCD for sequent processing.

Figure 3:
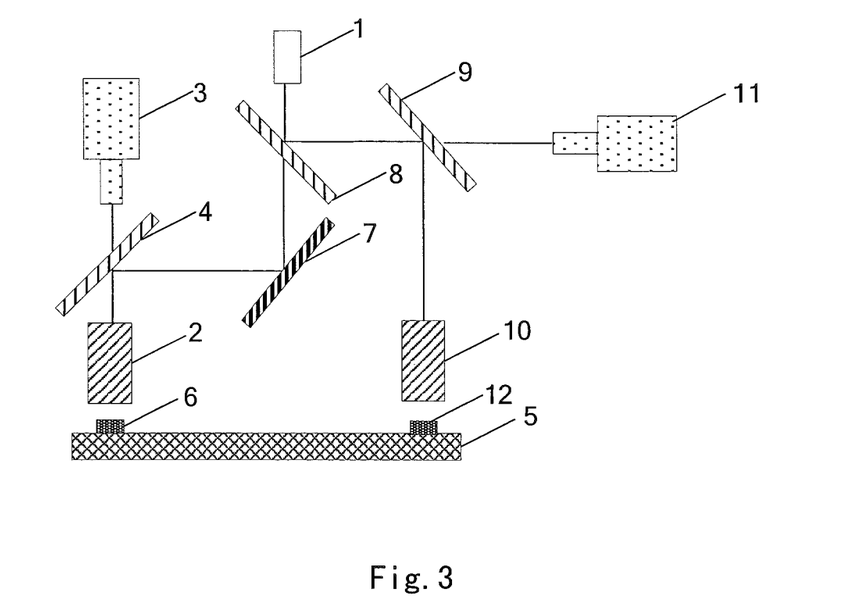
FIG. 3 is a schematic diagram showing a configuration of a further detection device according to an embodiment of the present invention.

Furthermore, referring to FIG. 3, if there are at least two ID figures on the substrate, the detection device further comprises a second light splitter or a second light splitting sheet 8, a third light splitter or a third light splitting sheet 9, a second image information acquisition unit 10, a second CCD 11, and a second analyzer. In the present embodiment, the second analyzer is integrated in the second CCD. Of course, a separate second analyzer may be disposed.

The second light splitter 8 is configured to split the light signal emitted from the light source 1 into the first light signal and a second light signal, and transmit the second light signal to the third light splitter 9.

Specifically, the second light splitter splits the light signal emitted from the light source into the first light signal and the second light signal so that two ID figures on the substrate can simultaneously obtain the light signals. Thus, the first CCD and the second CCD can simultaneously obtain the image light signals. As a result, the image light signals can be processed by the analyzer and the positions of the first ID figure and the second ID figure can be simultaneously analyzed.

The third light splitter 9 is configured to transmit the second light signal to the second image information acquisition unit.

The second image information acquisition unit 10 may be disposed over a second ID FIG. 12 on the substrate 5. The second image information acquisition unit 10 is configured to transmit the received second light signal onto the substrate 5, and to acquire a second image light signal generated by transmitting the second light signal onto both an edge of the second ID FIG. 12 on the substrate and the edge of the substrate 5, and transmit the second image light signal to the third light splitter 9.

The third light splitter 9 is further configured to transmit the second image light signal to the second CCD 11 so that the second CCD outputs a second electrical signal.

The second analyzer is configured to receive the second electrical signal outputted from the second CCD 11 and analyze wave crests of the second electrical signal, thereby obtaining a distance between the edge of the second ID FIG. 12 on the substrate 5 and the edge of the substrate 5.

Specifically, in the embodiment, the light source irradiates both the edge of the ID figures on the substrate and the edge of the substrate to generate the image signal. Then, the image signal is sent to the first CCD and the second CCD. The first CCD and the second CCD output the first and second electrical signals. The first and second analyzers can process light waves of the obtained images based on the first and second electrical signals. The difference between peak values of two wave crests of the light wave signals is obtained by calculation. In other words, the actual distance between the edge of the ID figure and the edge of the substrate can be obtained. If the difference between the peak values is within a preset range of standard value, then the entire product line where the detection device is disposed operates normally, and no abnormal signal is fed back. If the difference between the peak values exceeds the preset range of standard value, then the detection device sends an abnormal signal to a mainframe. After the mainframe receives the abnormal signal, operation of the entire production line is stopped, and the production line is checked for specific failure. In another feasible solution, the first CCD and the second CCD may convert the obtained image light signals into the electrical signals and send the electrical signals to the mainframe (an example of the analyzers), and the mainframe performs relevant processing of the image light signals or the electrical signals.

Figure 4:
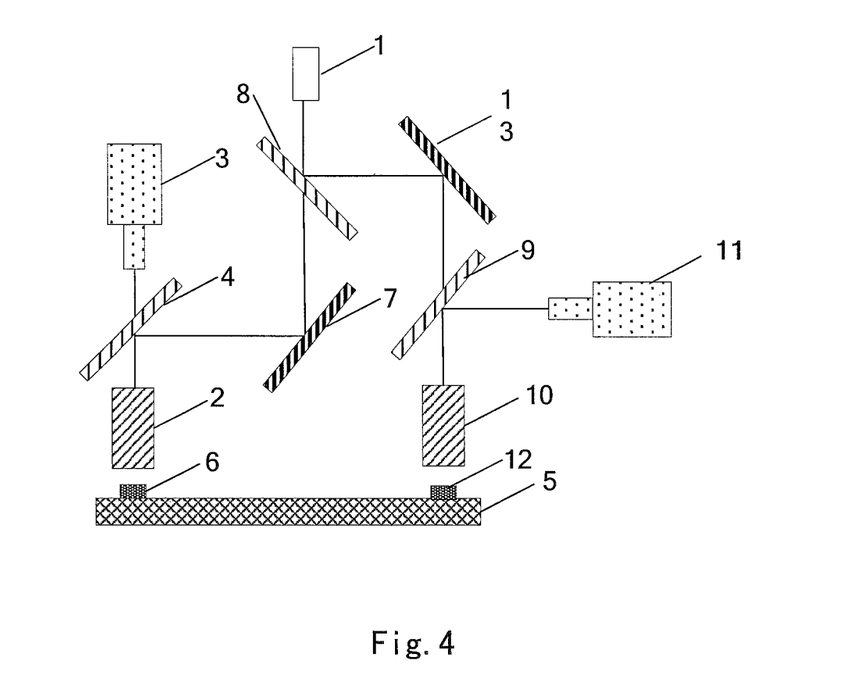
FIG. 4 is a schematic diagram showing a configuration of still another detection device according to an embodiment of the present invention.

In some embodiments, referring to FIG. 4, the detection device further comprises: a second reflecting mirror 13.

The second reflecting mirror 13 is configured to reflect the second light signal to the third light splitter 9 while filtering out interference light signals from the second light signal.

In the present embodiment, the second reflecting mirror has the similar function to the first reflecting mirror. For description of the second reflecting mirror, reference may be made to description of the first reflecting mirror in the above embodiment. The second reflecting mirror is no longer described for the sake of brevity.

In the present embodiment, the positions of the second light splitter, the third light splitter, and the second CCD are not limited to specific ones. FIGS. 3 and 4 only exemplary illustrate the positions of the second light splitter, the third light splitter, and the second CCD. In an actual application, the positions of the second light splitter, the third light splitter, and the second CCD may be any positions so long as they can accomplish their actual required functions.

By detecting the position of the ID figure on the substrate by the detection device according to the embodiment of the present invention instead of manual operation, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoid and the work efficiency is improved. Furthermore, the production rate can be improved.

In the present embodiment, the second image information acquisition unit may be any unit that can acquire image information and transmit the acquired image information. For example, the second image information acquisition unit may be any unit, such as a camera lens, commonly used in current actual production. In other words, the second image information acquisition unit may comprise a lens or a set of lenses.

Figure 5:
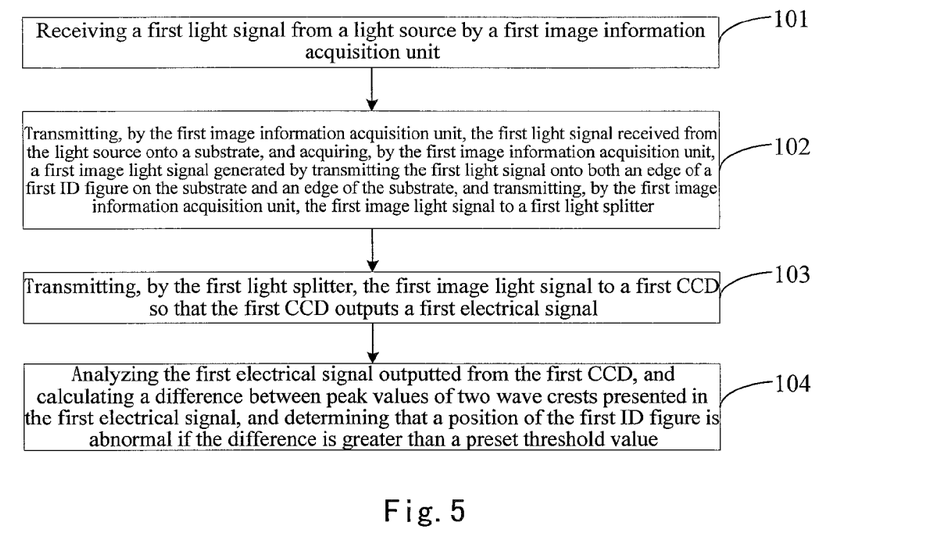
FIG. 5 is a schematic flow diagram of a detection method according to an embodiment of the present invention.

According to embodiments of the present invention, there is provided a detection method. As shown in FIG. 5, the detection method comprises:

step 101 of receiving a first light signal from a light source by a first image information acquisition unit;

step 102 of transmitting, by the first image information acquisition unit, the first light signal received from the light source onto a substrate, and acquiring, by the first image information acquisition unit, a first image light signal generated by transmitting the first light signal onto both an edge of a first ID figure on the substrate and an edge of the substrate, and transmitting, by the first image information acquisition unit, the first image light signal to a first light splitter;

step 103 of transmitting, by the first light splitter, the first image light signal to a first CCD so that the first CCD outputs a first electrical signal; and step 104 of analyzing the first electrical signal outputted from the first CCD, and calculating a difference between peak values of two wave crests presented in the first electrical signal, and determining that a position of the first ID figure is abnormal if the difference is greater than a preset threshold value. For example, the abnormal information is fed back to a terminal.

With the detection method according to the embodiment of the present invention, by detecting the position of the ID figure on the substrate by the detection device instead of pristine manual operation, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoid and the work efficiency is improved.

Figure 6:
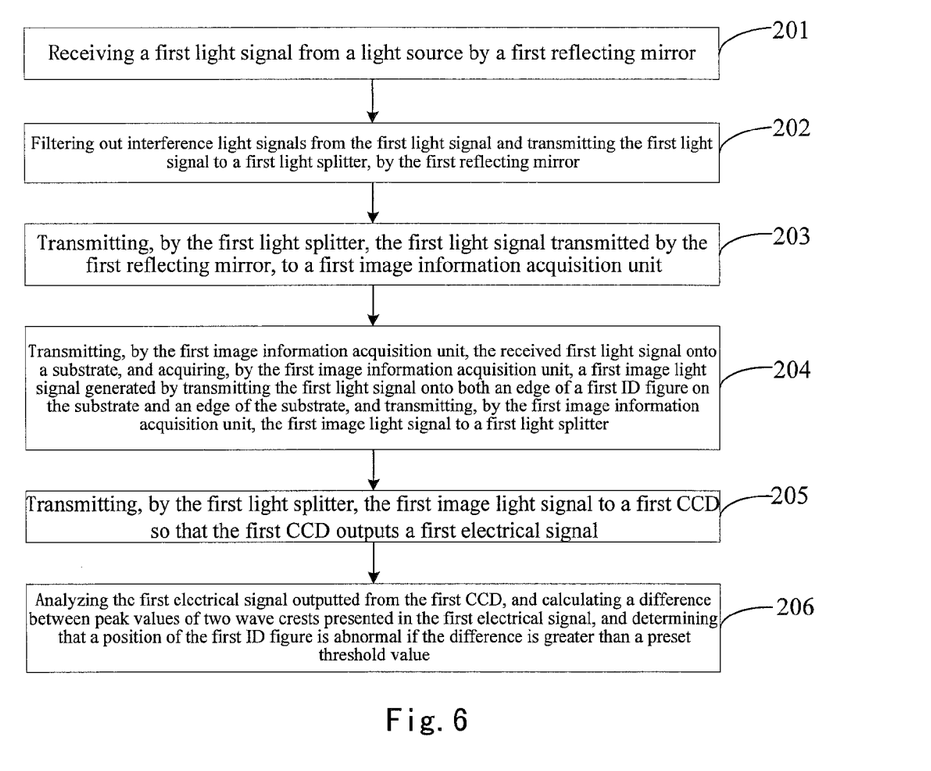
FIG. 6 is a schematic flow diagram of another detection method according to an embodiment of the present invention.

According to embodiments of the present invention, there is provided another detection method. As shown in FIG. 6, the detection method comprises:

step 201 of receiving a first light signal from a light source by a first reflecting mirror;

step 202 of filtering out interference light signals from the first light signal and transmitting the first light signal to a first light splitter, by the first reflecting mirror;

step 203 of transmitting, by the first light splitter, the first light signal transmitted by the first reflecting mirror, to a first image information acquisition unit;

step 204 of transmitting, by the first image information acquisition unit, the received first light signal onto a substrate, and acquiring, by the first image information acquisition unit, a first image light signal generated by transmitting the first light signal onto both an edge of a first ID figure on the substrate and an edge of the substrate, and transmitting, by the first image information acquisition unit, the first image light signal to a first light splitter;

step 205 of transmitting, by the first light splitter, the first image light signal to a first CCD so that the first CCD outputs a first electrical signal; and step 206 of analyzing the first electrical signal outputted from the first CCD, and calculating a difference between peak values of two wave crests presented in the first electrical signal, and determining that a position of the first ID figure is abnormal if the difference is greater than a preset threshold value. For example, the abnormal information is fed back to a terminal.

With the detection method according to the embodiment of the present invention, by detecting the position of the ID figure on the substrate by the detection device instead of pristine manual operation, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoid and the work efficiency is improved. Furthermore, the production rate can be improved.

Figure 7:
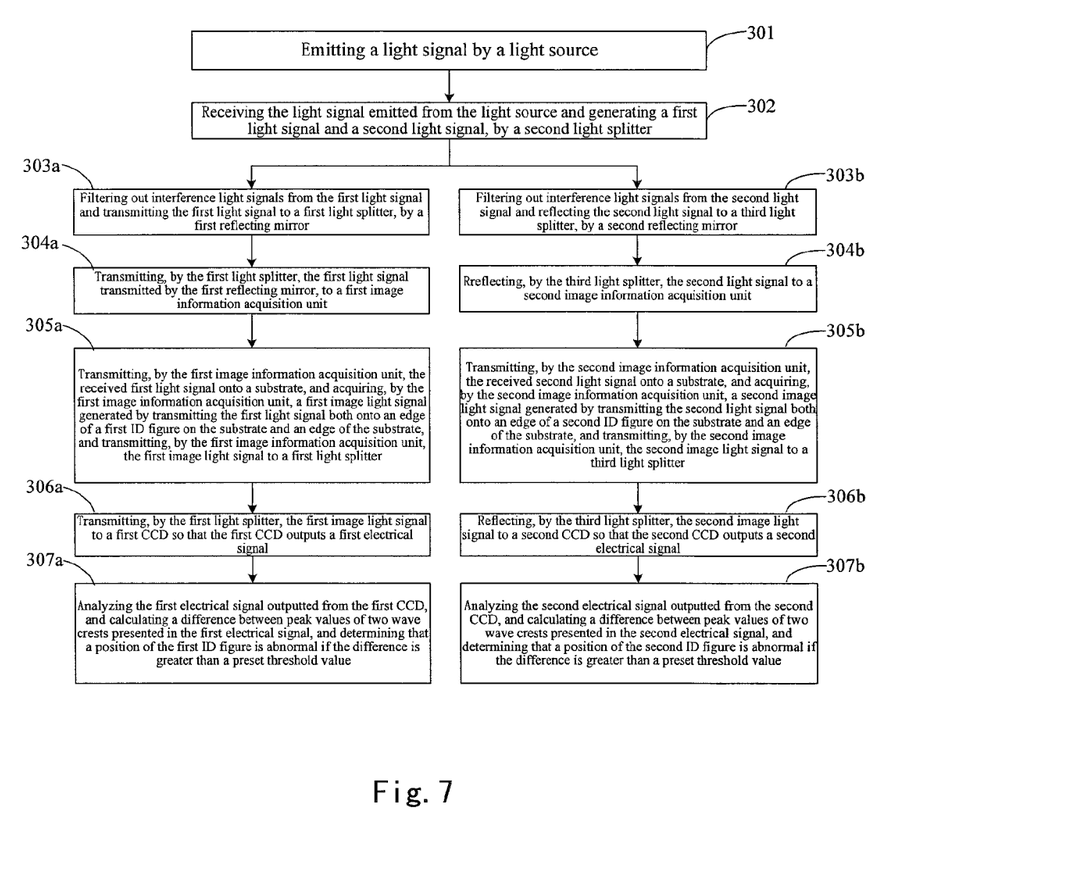
FIG. 7 is a schematic flow diagram of a further detection method according to an embodiment of the present invention.

According to embodiments of the present invention, there is provided a further detection method. As shown in FIG. 7, the detection method comprises:

step 301 of emitting a light signal by a light source;

step 302 of receiving the light signal emitted from the light source and generating a first light signal and a second light signal, by a second light splitter;

step 303a of filtering out interference light signals from the first light signal and transmitting the first light signal to a first light splitter, by a first reflecting mirror;

step 304a of transmitting, by the first light splitter, the first light signal transmitted by the first reflecting mirror, to a first image information acquisition unit;

step 305a of transmitting, by the first image information acquisition unit, the received first light signal onto a substrate, and acquiring, by the first image information acquisition unit, a first image light signal generated by transmitting the first light signal both onto an edge of a first ID figure on the substrate and an edge of the substrate, and transmitting, by the first image information acquisition unit, the first image light signal to a first light splitter;

step 306a of transmitting, by the first light splitter, the first image light signal to a first CCD so that the first CCD outputs a first electrical signal; and step 307a of analyzing the first electrical signal outputted from the first CCD, and calculating a difference between peak values of two wave crests presented in the first electrical signal, and determining that a position of the first ID figure is abnormal if the difference is greater than a preset threshold value. For example, the abnormal information is fed back to a terminal.

Furthermore, referring to FIG. 7, the detection method further comprises:

step 303b of filtering out interference light signals from the second light signal and reflecting the second light signal to a third light splitter, by a second reflecting mirror;

step 304b of reflecting, by the third light splitter, the second light signal to a second image information acquisition unit;

step 305b of transmitting, by the second image information acquisition unit, the received second light signal onto a substrate, and acquiring, by the second image information acquisition unit, a second image light signal generated by transmitting the second light signal both onto an edge of a second ID figure on the substrate and an edge of the substrate, and transmitting, by the second image information acquisition unit, the second image light signal to a third light splitter;

step 306b of reflecting, by the third light splitter, the second image light signal to a second CCD so that the second CCD outputs a second electrical signal; and step 307b of analyzing the second electrical signal outputted from the second CCD, and calculating a difference between peak values of two wave crests presented in the second electrical signal, and determining that a position of the second ID figure is abnormal if the difference is greater than a preset threshold value. For example, the abnormal information is fed back to a terminal.

It should be noted that the steps 303a-307a may be performed simultaneously with the steps 303b-307b, or may be performed before or after the steps 303b-307b. The order in which the steps 303a-307a and the steps 303b-307b are performed can be determined according to the specific application in actual performing of the steps.

With the detection method according to the embodiment of the present invention, by detecting the position of the ID figure on the substrate by the detection device instead of pristine manual operation, the technical problem is solved that when detecting whether or not a position of an ID figure on a substrate is offset, the ID figure is manually observed by human eyes, thereby generating a deviation or even an error in the detected position of the ID figure on the substrate. As a result, occurrence of production accident is avoid and the work efficiency is improved. Furthermore, the production rate can be improved.

Those skilled in the art will recognize that all or some of the steps achieving the above method according to the embodiment of the present invention can be performed by instructing a relevant hardware by a program. The program can be stored in a computer-readable storage medium comprising various mediums that can store program codes such as a ROM, a RAM, a disk or an optical disc. When the program is executed, the steps of the above method according to the embodiment of the present invention is performed.

The above embodiments are only used to explain the present invention, and should not be construed to limit the present invention. It will be understood by those skilled in the art that various changes and modifications may be made therein without departing from the spirit of the present invention, the scope of which is defined in the appended claims and their equivalents.

The invention claimed is:

1. A detection device, comprising:
a light source, a first image information acquisition unit, a first charge coupled device (CCD), a first light splitter, and a first analyzer, wherein:
the first image information acquisition unit is configured to receive a first light signal from the light source and transmit the first light signal onto a substrate, and to acquire a first image light signal generated by transmitting the first light signal onto both an edge of a first ID figure on the substrate and an edge of the substrate, and transmit the first image light signal to the first light splitter;

the first light splitter is configured to transmit the first image light signal to the first CCD so that the first CCD outputs a first electrical signal;

the first analyzer is configured to receive the first electrical signal outputted from the first CCD and analyze wave crests of the first electrical signal, thereby obtaining a distance between the edge of the first ID figure on the substrate and the edge of the substrate; and the detection device further comprising:
a first reflecting mirror, wherein:
the first light splitter is configured to receive the first light signal from the light source through the first reflecting mirror while the first reflecting mirror filters out interference light signals from the first light signal; and
the first light splitter is further configured to transmit the received first light signal to the first image information acquisition unit, the detection device further comprising:
a second light splitter, a third light splitter, a second Image Information acquisition unit, a second CCD, and a second analyzer, wherein:
the second light splitter is configured to split the light signal emitted from the light source into the first light signal and a second light signal, and transmit the second light signal to the third light splitter;
the third light splitter is configured to transmit the second light signal to the second image information acquisition unit;
the second image information acquisition unit is configured to transmit the received second light signal onto the substrate, and to acquire a second image light signal generated by transmitting the second light signal onto both an edge of a second ID figure on the substrate and an edge of the substrate, and transmit the second image light signal to the third light splitter;
the third light splitter is further configured to transmit the second image light signal to the second CCD so that the second CCD outputs a second electrical signal; and
the second analyzer is configured to receive the second electrical signal outputted front the second CCD and analyze wave crests of the second electrical signal, thereby obtaining a distance between the edge of the second ID figure on the substrate and the edge of the substrate.

2. The detection device of claim 1, further comprising: a second reflecting mirror configured to reflect the second light signal to the third light splitter while filtering out interference light signals from the second light signal.

3. The detection device of claim 1, wherein the first image information acquisition unit comprises a lens.

4. The detection device of claim wherein the second image information acquisition unit comprises a lens.

5. A detection method, comprising:
receiving a first light signal from a light source by a first image information acquisition unit;
transmitting, by the first image information acquisition unit, the first light signal received from the light source onto a substrate, and acquiring, by the first image information acquisition unit, a first image light signal generated by transmitting the first light signal onto both an edge of a first ID figure on the substrate and an edge of the substrate, and transmitting, by the first image information acquisition unit, the first image light signal to a first light splitter;

transmitting, by the first light splitter, the first image light signal to a first CCD so that the first CCD outputs a first electrical signal;

analyzing the first electrical signal outputted from the first CCD, and calculating a difference between peak values of two wave crests presented in the first electrical signal, and if the difference is greater than a preset threshold value, then it is determined that a position of the first ID figure is abnormal;

the receiving the first light signal from the light source comprising:
filtering out interference light signals from the first light signal and transmitting the first light signal to a first light splitter, by a first reflecting mirror; and transmitting, by the first light splitter, the first light signal transmitted by the first reflecting mirror to the first image information acquisition unit; and further comprising:
splitting, by a second light splitter, the light signal emitted from the light source into the first light signal and a second light signal;
transmitting, by a third light splitter, the second light signal to a second image information acquisition unit;
transmitting, by the second image information acquisition unit, the received second light signal onto the substrate, and acquiring, by the second image information acquisition unit, a second image light signal generated by transmitting the second light signal onto both an edge of a second ID figure on the substrate and an edge of the substrate, and transmitting, by the second image information acquisition unit, the second image light signal to the third light splitter;
transmitting, by the third light splitter, the second image light signal to the second CCD so that the second CCD outputs a second electrical signal; and
analyzing the second electrical signal outputted from the second CCD, and calculating a difference between peak values of two wave crests presented in the second electrical signal, and, determining that a position of the second ID figure is abnormal if the difference is greater than the preset threshold value.

6. The detection method of claim 5, further comprising: filtering out interference light signals from the second light signal and then reflecting the second light signal to the third light splitter, by the second reflecting mirror.

7. The detection method of claim 5, further comprising: outputting abnormal information to a terminal if it is determined that the position of the first ID figure is abnormal.

8. The detection method of claim 5, further comprising: outputting abnormal information to a terminal if it is determined that the positions of the first and second ID figures are abnormal.

9. The detection method of claim 5, wherein:
the first image information acquisition unit comprises a lens.

10. The detection method of claim 5, wherein:
the second image information acquisition unit comprises a lens.

* * * * *